(12) United States Patent
Liu et al.

(10) Patent No.: US 9,745,385 B2
(45) Date of Patent: Aug. 29, 2017

(54) ANTHROPOGENIC INSECT-RESISTANT GENE AND CRY1C TOXIN IDIOTYPE SINGLE-CHAIN ANTIBODY ENCODED THEREBY AND APPLICATION THEREOF

(71) Applicant: JIANGSU ACADEMY OF AGRICULTURAL SCIENCES, Jiangsu (CN)

(72) Inventors: Xianjin Liu, Jiangsu (CN); Chongxin Xu, Jiangsu (CN); Xiao Zhang, Jiangsu (CN); Yuan Liu, Jiangsu (CN); Yajing Xie, Jiangsu (CN); Cunzheng Zhang, Jiangsu (CN); Xiangyang Yu, Jiangsu (CN); Donglan Wang, Jiangsu (CN)

(73) Assignee: JIANGSU ACADEMY OF AGRICULTURAL SCIENCES, Jiangsu (CN)

( * ) Notice: Subject to any disclaimer, the term of this patent is extended or adjusted under 35 U.S.C. 154(b) by 0 days.

(21) Appl. No.: 15/025,805

(22) PCT Filed: Jan. 9, 2015

(86) PCT No.: PCT/CN2015/070422
§ 371 (c)(1),
(2) Date: Mar. 29, 2016

(87) PCT Pub. No.: WO2015/109953
PCT Pub. Date: Jul. 30, 2015

(65) Prior Publication Data
US 2016/0215066 A1    Jul. 28, 2016

(30) Foreign Application Priority Data

Jan. 26, 2014    (CN) .......................... 2014 1 0037240

(51) Int. Cl.
*C07K 16/42*    (2006.01)
*A01N 63/02*    (2006.01)
*C07K 16/12*    (2006.01)
*A01N 57/16*    (2006.01)

(52) U.S. Cl.
CPC .......... *C07K 16/4233* (2013.01); *A01N 57/16* (2013.01); *A01N 63/02* (2013.01); *C07K 16/1278* (2013.01); *C07K 2317/622* (2013.01); *C07K 2317/76* (2013.01)

(58) Field of Classification Search
None
See application file for complete search history.

(56) References Cited

U.S. PATENT DOCUMENTS

2004/0221334 A1    11/2004    Baum et al.

FOREIGN PATENT DOCUMENTS

CN    102936598 A    2/2013

OTHER PUBLICATIONS

Wang, Yun et al., "Isolation of single chain variable fragment (scFv) specific for Cry1C toxin from human single fold scFv libraries," *Toxicon*, Sep. 2012, 60:1290-1297.
Wang, Yun et al., "Screening of anti-Cry1Ac scFv from a Phage display antibody library," *Chinese Journal of Cellular and Molecular Immunology*, Dec. 2009; 25(12): Abstract.

*Primary Examiner* — Addison D Ault
(74) *Attorney, Agent, or Firm* — Saliwanchik, Lloyd & Eisenschenk

(57) ABSTRACT

An anthropogenic insect-resistant gene having a nucleotide sequence represented by SEQ ID NO.1, and a Cry1C toxin idiotype single-chain antibody encoded by said anthropogenic insect-resistant gene and having an amino acid sequence represented by SEQ ID NO.2; the antibody is a β-type and has insecticidal activity, and after expression by the prokaryotic system, the primary culture thereof has binding activity to *Cnaphalocrocis medinalis* midgut peritrophic membrane specific receptor BBMV; the β-type Cry1C toxin idiotype single-chain antibody of the present invention is obtained without animal immunization, has a short preparation period and small amino acid sequence, and is suitable for large-scale in vitro production. The present invention is an entirely new insect-resistant gene resource, and has significant implications for decreasing the various safety risks associated with the widescale use of existing Bt toxins, substituting Bt toxins in the biocontrol of agricultural pests, and reducing the use of pesticides.

5 Claims, 2 Drawing Sheets

SEQUENCE LISTING

```
<160> NUMBER OF SEQ ID NOS: 2

<210> SEQ ID NO 1
<211> LENGTH: 843
<212> TYPE: DNA
<213> ORGANISM: Artificial
<220> FEATURE:
<223> OTHER INFORMATION: human-derived insect-resistant gene

<400> SEQUENCE: 1
tctatttcaa ggagacagtc ataatgaaat acctattgcc tacggcagcc gctggattgt      60
tattactcgc ggcccagccg gccatggccg aggtgcagct gttggagtct gggggaggct     120
tggtacagcc tgggggtcc ctgagactct cctgtgcagc ctctggattc acctttagca     180
gctatgccat gagctgggtc cgccaggctc cagggaaggg gctggagtgg gtctcatcga     240
ttagtaagca tggtagtagg acaacttacg cagactccgt gaagggccgg ttcaccatct     300
ccagagacaa ttccaagaac acgctgtatc tgcaaatgaa cagcctgaga gccgaggaca     360
cggccgtata ttactgtgcg aaacggagta ggctgtttga ctactgggc cagggaaccc     420 tggtcaccgt ctcgagcggt ggaggcggtt caggcggagg tggcagcggc ggtggcgggt     480
cgacggacat ccagatgacc cagtctccat cctccctgtc tgcatctgta ggagacagag     540
tcaccatcac ttgccgggca agtcagagca ttagcagcta tttaaattgg tatcagcaga     600
aaccagggaa agcccctaag ctcctgatct atcatgcatc ccacttgcaa agtggggtcc     660
catcaaggtt cagtggcagt ggatctggga cagatttcac tctcaccatc agcagtctgc     720
aacctgaaga ttttgcaact tactactgtc aacagcggca tcagcggcct cggacgttcg     780
gccaagggac caaggtggaa atcaaacggg cggccgcaca tcatcatcac catcacgggg     840
ccg                                                                   843

<210> SEQ ID NO 2
<211> LENGTH: 291
<212> TYPE: PRT
<213> ORGANISM: Artificial
<220> FEATURE:
<223> OTHER INFORMATION: amino acid sequence of screened anti-CrylC
      toxin idiotype single-chain antibody

<400> SEQUENCE: 2

Met Lys Tyr Leu Leu Pro Thr Ala Ala Ala Gly Leu Leu Leu Leu Ala
1               5                   10                  15
```

```
Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ser Ile Ser Lys His Gly Ser Arg Thr
65                  70                  75                  80

Thr Tyr Ala Asp Ser Val Lys Gly Arg Phe Thr Ile Ser Arg Asp Asn
            85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Arg Ser Arg Leu Phe Asp Tyr Trp
            115                 120                 125

Gly Gln Gly Thr Leu Val Thr Val Ser Ser Gly Gly Gly Gly Ser Gly
        130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr His Ala Ser His Leu
            195                 200                 205

Gln Ser Gly Val Pro Ser Arg Phe Ser Gly Ser Gly Ser Gly Thr Asp
        210                 215                 220

Phe Thr Leu Thr Ile Ser Ser Leu Gln Pro Glu Asp Phe Ala Thr Tyr
225                 230                 235                 240

Tyr Cys Gln Gln Arg His Gln Arg Pro Arg Thr Phe Gly Gln Gly Thr
            245                 250                 255

Lys Val Glu Ile Lys Arg Ala Ala Ala His His His His His His Gly
            260                 265                 270

Ala Ala Glu Gln Lys Leu Ile Ser Glu Glu Asp Leu Asn Gly Ala Ala
            275                 280                 285

Ser Thr Pro
    290
```

ANTHROPOGENIC INSECT-RESISTANT GENE AND CRY1C TOXIN IDIOTYPE SINGLE-CHAIN ANTIBODY ENCODED THEREBY AND APPLICATION THEREOF

CROSS REFERENCE TO A RELATED APPLICATION

This application is a National Stage Application of International Application Number PCT/CN2015/070422, filed Jan. 9, 2015; which claims priority to Chinese Patent Application No. 201410037240.9, filed Jan. 26, 2014; both of which are incorporated herein by reference in their entirety.

The Sequence Listing for this application is labeled "SeqList-15Mar16-ST25.txt," which was created on Mar. 15, 2016, and is 5 KB. The entire content is incorporated herein by reference in its entirety.

FIELD OF THE INVENTION

The present invention relates to genetic engineering and biological control field, particularly to a human-derived insect-resistant gene and anti-Cry1C toxin idiotype single-chain antibody encoded thereby and application thereof.

BACKGROUND OF THE INVENTION

Currently, the insecticidal gene widely used in the world for biological control of pests is Bt toxin gene of *Bacillus thuringiensis* (Bt) (such as: Cry1C, Cry1Ab, Cry1B and Cry1F et al.). *Bacillus thuringiensis* is an insect pathogenic bacterium. The Bt toxin generated by *Bacillus thuringiensis* has a specific killing effect to many species of agricultural and forestry pests. Since Belgian Plant Genetic Systems first reported the success of transgenic Bt insect-resistant tobacco in 1987 till today, Bt gene has been transferred into main crops in the world, such as: maize, paddy, cotton, tomato, potato and tobacco. According to the statistics of International Service for the Acquisition of Agri-biotech Applications (ISAAA) in 2012, the area of transgenic Bt cotton grown in China has exceeded 3.9 million hectares, accounting for 71.5% of the total area of the cotton grown in China. However, following the application and popularization of transgenic Bt crops, its possible potential hazards in gene escape, change of microbial ecological structure of soil, drug resistance of species and harm to normal immune system have gradually received the attention of the society. The document entitled "Diversity of Rhizospheric Microorganisms and Bacterial Physiological Groups of Transgenic Bt Maize" (Min Wang et al., Chinese Journal of Ecology, 2010(03)) and "Influence of Transgenic Bt Maize on Bacterial Quantity Diversity of Soil" (Ling Liu et al., Journal of Ecology and Rural Environment, 2011(03)) analyzed the bacterial quantity and diversity of the soil in which transgenic Bt maize is grown indoors and outdoors respectively. The results all show significant difference between the transgenic Bt maize group and the blank control group.

The document "Cry1Ac protoxin from *Bacillus thuringiensis* sp. *kurstaki* HD73 binds to surface proteins in the mouse small intestine" (Vázquez-Padrón et al., Biochem Biophys Res Commun, 2000(01)) disclosed that, in animal experiment, when intrinsic toxic protein of Bt and extrinsic toxic protein of Bt taken in by a mouse reached 10 mg/kg and 100 mg/kg respectively, T cell ANAE positive rate, spleen index and macrophage phagocytosis of the mouse all were inhibited obviously. The more doses are intaken, the more obvious the inhibiting effect will be. This experiment also discovered that when the cumulative coefficient of Bt toxin protein in animal body was greater than 6.24, it might result in injury of liver, kidney and gastrointestinal tract etc. and in liver and kidney, anomalies of cellular swelling and vacuolar degeneration could be observed and glomerular vascular epithelial lesion could be seen. Of course, it can't be excluded that they were caused by immunoreactions. Meanwhile, long-term use of Bt toxin protein at a large dose may also result in significant decrease of total white blood cells (WBC) number and hemoglobin (HGB) content of animals. This also indicates that Bt toxin protein has obvious toxicity of immunosuppression. Therefore, developing substitute biological effectors with Bt toxin bioactivity (such as: anti-idiotype antibody) is a research hotspot in biological pesticide development field.

In 1974, Danish immunologist Jerne firstly proposed the concept of anti-idiotype antibody in his "Immune Network Theory". Anti-idiotype antibody (hereinafter referred to as "Anti-Id") refers to the specific antibody generated directed to the idiotype (hereinafter referred to as "Id") in the variable regions of antibody molecules. Bona, et al. classified Anti-Id into four types ($\alpha$, $\beta$, $\gamma$ and $\epsilon$) based on serological reaction between Id and Anti-Id as well as the function of AId. $\beta$-type Anti-Id has the effect of "internal image", i.e.: has antigenic determinant same as (haptin) antigen, so it may have the function and bioactivity of antigen.

Currently, it is universally believed that Anti-Id with an effect similar to target antigen may be obtained by phage display technology through establishment of a phage antibody library, and specific screening. The process of screening specific antibody by phage display technology is called "Panning" and mainly includes four steps: binding, washing, eluting and amplification. Raats et al. adopted anti-cortisol monoclonal antibody envelope as solid-phase antigen for direct screening. Before screening, a same species of negative monoclonal antibody is used to perform negative screening to avoid screening recombinant antibody fragments bound to the constant region of antibody and successfully screen Anti-Id against cortisol. Goletz et al. also employed phage antibody display system and researched and compared the influence of different elution methods on Anti-Id fragment screening results. Of the eventually screened 96 clones, 28 were positive clones with Anti-Id characteristics. So far, no related materials and products specific to substitutable Bt active effector, particularly Anti-Bt toxin type Anti-Id single-chain antibody (hereinafter referred to as "Anti-Id ScFvs"), have been reported.

SUMMARY OF THE INVENTION

To address the potential safety hazard, hypersensitivity and other problems from the extensive application of transgenic Bt toxin crops and toxin preparations thereof at present, developing a substitutable biological effector with Bt toxin bioactivity, and its application in biological control of pests, the present invention is realized in the following way:

A human-derived insect-resistant gene, having a nucleotide sequence represented by SEQ ID NO.1;

In the present invention, an anti-Cry1C toxin idiotype single-chain antibody encoded by SEQ ID NO.1, having an amino acid sequence represented by SEQ ID NO.2;

In the present invention, a prokaryotic expression vector containing human-derived insect-resistant gene of SEQ ID NO.1;

In the present invention, an application of human-derived insect-resistant gene of SEQ ID NO.1 in control of agricultural pests;

In the present invention, an insecticide containing anti-Cry1C toxin idiotype single-chain antibody with an amino acid sequence as represented by SEQ ID NO.2.

In the present invention, a "β"-type anti-Cry1C toxin idiotype single-chain antibody with insecticidal activity is screened and obtained from disclosed human gene banks. After expression by the prokaryotic system, the primary culture of this single-chain antibody has binding activity to *Cnaphalocrocis medinalis* midgut peritrophic membrane specific receptor BBMV. The present invention obtains "β"-type anti-Cry1C toxin idiotype single-chain antibody without animal immunization. The preparation cycle is short. The amino acid sequence is small. It is suitable for in vitro mass production. Meanwhile, as a new insect-resistant gene resource, the present invention has important scientific and practical significance to exploring and developing new-type insect-resistant gene resources simulating Bt toxin bioactivity to lower the safety risks from the wide use of existing Bt toxins and even substitute Bt in the future in biological control of agricultural pests and reduce the use of pesticides.

DETAILED DESCRIPTION OF THE EMBODIMENTS

Embodiment 1: Screening Human-Derived Inset-Resistant Gene

Figure 1:
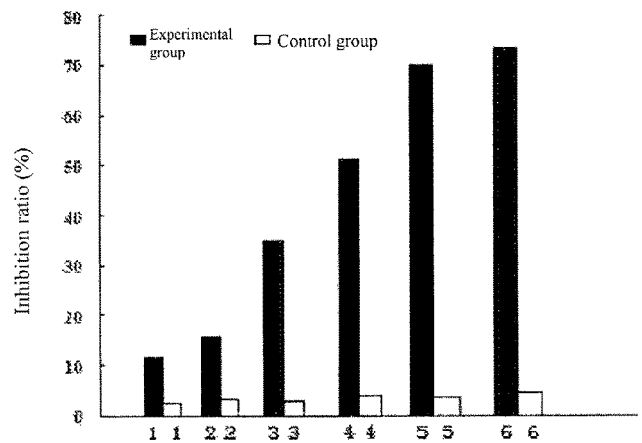
FIG. 1 is a schematic of E8 ELISA detection result.

Reagents and Medium Formulae Involved in the Embodiment (1) 2×TY liquid medium:
Add 16 g of tryptone, 10 g of yeast extract and 5 g of NaCl in 900 mL of double distilled water, mix them well, set the volume to 1 L by double distilled water, put the liquid in an autoclave, sterilize it at 121° C. for 20 min, cool it and store it at 4° C. for future use.

(2) 2×TY-AG liquid medium:
Add ampicillin with final concentration of 100 μg/ml and glucose with a mass ratio of 1% to 2×TY culture medium.

(3) 2×TY-AK liquid medium:
Add ampicillin with final concentration of 100 μg/ml and kanamycin with final concentration of 50 μg/ml to 2×Ty culture medium.

(4) 2×TY-AKG liquid medium:
Add ampicillin with final concentration of 100 μg/ml, kanamycin with final concentration of 50 μg/ml and glucose with a mass ratio of 1% to 2×TY culture medium.

(5) TYE solid medium:
Add 15.0 g of agarose, 8 g of NaCl, 10 g of tryptone and 5 g of yeast extract in 900 ml of double distilled water, set the volume to 1 L by double distilled water, put the liquid in an autoclave, sterilize it at 12° C. for 20 min, cool it and store it at 4° C. for future use.

(6) TYE-AG solid medium:
Add ampicillin with final concentration of 100 μg/ml and glucose with a mass ratio of 1% to TYE solid medium.

(7) PBS solution
Weigh 8.0 g of NaCl, 0.2 g of KCl, 2.9 g of $Na_2HPO_4.12H_2O$ and 0.2 g of $KH_2PO_4$, add them in distilled water respectively, dissolve them thoroughly and set the volume to 1 L.

(8) PBST solution
Add Tween-20 with a volume ratio of 0.05% to PBS solution.

(9) PEG/NaCl solution:
Weigh 20 g of PEG 8000 and 14.61 g of NaCl, add them to 80 ml of deionized water, set the volume to 100 ml, put the solution in an autoclave, sterilize it at 121° C. for 20 min, cool it and store it at 4° C. for future use.

(10) Citrate buffer solution (CPBS, substrate buffer solution, pH=5.5):
Weigh 21 g of $C_6H_7O_8$ (citric acid) and 71.6 g of $Na_2HPO_4.12H_2O$, add them to distilled water respectively, dissolve them thoroughly and set the volume to 1 L.

(11) Tetramethyl benaidine (TMB) solution:
Weigh 10 mg of TMB, dissolve it in 1 ml of dimethyl sulfoxide, keep the solution in a dark place and store it at 4° C. for future use.

(12) Substrate chromogenic solution:
Components of 10 ml formula: 9.875 ml of CPBS, 100 μl of TMB solution and 25 μl of $H_2O_2$ with volume ratio of 20%.

Sources of the materials involved in the embodiment:
Anti-Cry1C polyclonal antibody, BBMV, irrelevant Anti-Id single-chain antibody, non-"β"-type Anti-Id ScFv, cabbage leaves and *Plutella xylostella* third instar larvae were provided by the Key Laboratory for Agricultural Product Quality and Safety Control Technology and Standard of the Ministry of Agriculture, Jiangsu Academy of Agricultural Sciences;

Human-derived phage antibody library, TG1 bacteria and helper phage KM13 were purchased from British Source BioScience;

HRP-goat-anti-M13-IgG was purchased from Wuhan Boster Co., Ltd.;

Cry1C toxin and Cry1Ab toxin were purchased from Shanghai Youlong Biotech Co., Ltd.;

Paddy leaves and *Cnaphalocrocis medinalis* third instar larvae were provided by Yangzhou Luyuan Bio-Chemical Co., Ltd.

Embodiment 1: Screen Anti-Cry1C Toxin Idiotype Single-Chain Antibody (1) Add 20 μl of human-derived phage antibody library bacterium liquid to 200 ml of 2×TY-AG liquid medium, cultivate it at constant temperature 37° C. till $OD_{600}$ reaches 0.4, measure 50 ml of the bacterium liquid, add $1 \times 10^{12}$ pfu of helper phage KM13 for superinfection, incubate the obtained solution at 37° C. for 30 min, then centrifuge it at 3300 g for 10 min, discard the supernate, use 100 ml of 2×TY-AKG liquid medium to resuspend and precipitate it and cultivate it at 30° C. overnight;

centrifuge it at 3300 g for 30 min next day, collect the supernate, add 20 ml of PEG/NaCl solution, keep it in ice bath for 1 h, then centrifuge it at 3300 g for 30 min and resuspend and precipitate it by 4 ml of PBS; centrifuge the resuspension solution at 11600 g for 10 min. The supernate is amplified phage antibody library;

(2) Use the amplified phage antibody library obtained in step 1 for four rounds of panning: in the first round of panning, coat 4 ml of 100 µg/ml anti-Cry1C polyclonal antibody to the bottom of a cell culture flask, keep it at 4° C. overnight, wash the cell culture flask with 1 ml of PBS for 3 times next day, then add 1 ml of thoroughly mixed amplified phage antibody library and 4 ml of 3% MPBS solution, put the flask on a shaker, slowly shake it at room temperature for 1 h, let it rest for 1 h, remove the liquid in the culture flask, wash the flask with 1 ml of PBST solution for 20 times and add 1 ml of 10 mg/ml trypsin to elute the specifically bound phage antibody. The eluent is phage antibody obtained in the first round of panning. The concentrations of the coated anti-Cry1C polyclonal antibody panned in the second, third and fourth rounds are 50 µg/ml, 25 µg/ml and 10 µg/ml respectively. The used phage antibody is the phage antibody obtained from the previous round of panning. The panning method is same as that adopted in the first round. 10 µl of the phage antibody panned in the fourth round is used to infect 1 ml of TG1 bacteria in a logarithmic phase. After it is incubated at 37° C. for 1 h, it is coated on TYE-AG solid medium and cultivated at 37° C. overnight; next day, single colonies are picked randomly, incubated on a 96-well plate containing 100 µl/well of 2×TY-AG liquid medium and cultivated at 37° C. overnight; next day, 2 µl of bacterium liquid is sucked from the well plate, transferred to a new 96-well plate and incubated at 37° C. for 2 h. 25 µl of helper phage KM13 with titer of $10^{12}$ is added to each well, incubated at 30° C. for 2 h, centrifuged at 1800 g for 10 min, resuspended and precipitated with 150 µl of 2×TY-AK liquid medium and then cultivated at 30° C. overnight. Next day, it is centrifuged at 1800 g for 30 min. The supernate is collected;

(3) 4 µg/ml anti-Cry1C polyclonal antibody is taken and added to a 96-well plate at a concentration of 100 µl/well, and stored at 4° C. overnight. Next day, 100 µl of the supernate obtained in step 2 is added to each well. 100 µl of 2×TY-AK liquid medium is added to the negative control. They are kept in 37° C. water bath for 2 h. After the plate is washed with 250 µ/well of PBST, 100 µl of 1:5000 diluted HRP-goat-anti-M13-IgG is added to each well and incubated at 37° C. for 2 h. 100 µl of substrate chromogenic solution is added to each well and takes reaction at room temperature for 10 to 20 min till blue appears. Lastly 500 of 2 mol/L $H_2SO_4$ is added to each well to quickly terminate the reaction. $OD_{450}$ is determined by ELIASA. If $OD_{450}$ of the solution/$OD_{450}$ of negative control is greater than 2.1, it will be judged as positive. The supernate in step 2 corresponding to this solution is the screened supernate containing anti-Cry1C toxin Idiotype single-chain antibody.

The nucleotide sequence of the screened anti-Cry1C toxin idiotype single-chain antibody determined by Sanger sequencing method is SEQ ID NO.1, as shown below:

```
tctatttcaa ggagacagtc ataatgaaat acctattgcc tacggcagcc gctggattgt    60
tattactcgc ggcccagccg gccatggccg aggtgcagct gttggagtct gggggaggct   120
tggtacagcc tgggggggtcc ctgagactct cctgtgcagc ctctggattc acctttagca   180
gctatgccat gagctgggtc cgccaggctc cagggaaggg gctggagtgg gtctcatcga   240
ttagtaagca tggtagtagg acaacttacg cagactccgt gaagggccgg ttcaccatct   300
ccagagacaa ttccaagaac acgctgtatc tgcaaatgaa cagcctgaga gccgaggaca   360
cggccgtata ttactgtgcg aaacggagta ggctgtttga ctactggggc cagggaaccc   420
tggtcaccgt ctcgagcggt ggaggcggtt caggcggagg tggcagcggc ggtggcgggt   480
cgacggacat ccagatgacc cagtctccat cctccctgtc tgcatctgta ggagacagag   540
tcaccatcac ttgccgggca agtcagagca ttagcagcta tttaaattgg tatcagcaga   600
aaccagggaa agcccctaag ctcctgatct atcatgcatc ccacttgcaa agtggggtcc   660
catcaaggtt cagtggcagt ggatctggga cagatttcac tctcaccatc agcagtctgc   720
aacctgaaga ttttgcaact tactactgtc aacageggca tcagcggcct cggacgttcg   780
gccaagggac caaggtggaa atcaaacggg cggccgcaca tcatcatcac catcacgggg   840
ccg                                                                  843
```

After nucleotide translation, the amino acid sequence of screened anti-Cry1C toxin idiotype single-chain antibody determined by Sanger sequencing method is SEQ ID NO.2, as shown below:

```
                                                    H-CDR1
          MKYLLPTAAAGLLLLAAQPAMAEVQLLESGGGLVQPGGSLRLSCAASGFTFSSYAMSWVR      60

H-CDR2
          QAPGKGLEWVSSISKHGSRTTYADSVKGRFTISRDNSKNTLYLQMNSLRAEDTAVYYCAK    120
```

```
        H-CDR1                -----Link-----
RSRLFDYWGQGTLVTVSSGGGGSGGGGSGGGGSTDIQMTQSPSSLSASVGDRVTITCRAS            180

L-CDR1                   L-CDR2
QSISSYLNWYQQKPGKAPKLLIYHASHLQSGVPSRFSGSGSGTDFTLTISSLQPEDFATY            240

L-CDR3                    His-tag
YCQQRHQRPRTFGQGTKVEIKRAAAHHHHHHGAAEQKLISEEDLNGAASTP                     291
```

The applicant names this anti-Cry1C toxin idiotype single-chain antibody as E8.

Embodiment 2: Prepare Primary Culture of E8

The supernate obtained containing anti-Cry1C toxin idiotype single-chain antibody screened in Embodiment 1 is transferred to 10 ml of 2×TY-AG liquid medium at a volume ratio of 1:100 and incubated at 37° C. for 2 h. 100 μl of helper phage KM13 with titer of $10^{12}$ is added for rescue, incubated at 30° C. for 2 h and centrifuged at 1800 g for 10 min. The supernate is removed. 2×TY-AK liquid medium is used to resuspend and precipitate the bacteria. It is cultivated while being shaken at 30° C., 250 rpm overnight. Next day it is centrifuged at 1800 g for 30 min. Its supernate is supernate containing E8 primary culture.

Embodiment 3: Subtype Identification of E8

(1) ELISA Detection Experiment of Competitive Inhibition

The experiment adopts 6 experimental groups and corresponding control groups. Solutions are prepared based on Table 1.

TABLE 1

Preparation of solutions for competitive inhibition ELISA detection experiment

| Group | E8 | Irrelevant Anti-Id single-chain antibody | 2 × TY liquid medium |
|---|---|---|---|
| Experimental group 1 | 5 μl | | 45 μl |
| Control group 1 | | 5 μl | 45 μl |
| Experimental group 2 | 10 μl | | 40 μl |
| Control group 2 | | 10 μl | 40 μl |
| Experimental group 3 | 20 μl | | 30 μl |
| Control group 3 | | 20 μl | 30 μl |
| Experimental group 4 | 30 μl | | 20 μl |
| Control group 4 | | 30 μl | 20 μl |
| Experimental group 5 | 40 μl | | 10 μl |
| Control group 5 | | 40 μl | 10 μl |
| Experimental group 6 | 50 μl | | |
| Control group 6 | | 50 μl | |

In Table 1, E8 is the supernate containing E8 primary culture obtained in Embodiment 2.

Add 50 μl of 10 μg/ml anti-Cry1C polyclonal antibody to the solutions prepared according to Table 1 respectively, incubate them at 37° C. for 2 h, add them to a 96-well plate coated with 2 μg/ml Cry1C toxin respectively (the 96-well plate coated with 2 μg/ml Cry1C toxin is obtained by adding 2 μg/ml Cry1C toxin to a 96-well plate on the previous day at a concentration of 100 μl/well and keeping it at 4° C. overnight), take reaction for 2 h; wash the plate with 250 μg/well of PBST for 3 times, add 100 μl/well of 1:5000 diluted HRP-goat anti-rabbit IgG, incubate it at room temperature for 1 h; wash the plate with 250 μl/well of PBST for 3 times, add 100 μg/well of substrate chromogenic solution, take reaction at room temperature for 10 to 20 min till blue appears and in the end add 50 μl/well of 2 mol/L $H_2SO_4$ to quickly terminate the reaction; determine $OD_{450}$ by ELIASA.

The experimental results are shown in FIG. 1. The inhibition ratio increases with the increase of E8 content. The control groups do not have the phenomenon of competitive inhibition, suggesting E8 is β-type Anti-Id single-chain antibody and can simulate Cry1C toxin to competitively bind with anti-Cry1C toxin polyclonal antibody.

(2) Biological Determination Experiment

The experiment has experimental group 1, experimental group 2, experimental group 3, positive control group, negative control group 1, negative control group 2 and negative control group 3; the experimental procedure is as follows:

(a) Blocking: Coat 100 μg/well of 5 μg/ml BBMV in a 96-well plate, keep it at 4° C. overnight, wash the plate with 250 μl/well of PBST for 3 times next day, add 200 μl/well of BAS with a mass ratio of 3% respectively, incubate it at room temperature for 2 h, and carry out blocking;

(b) Sample addition: Wash the 96-well plate blocked in step 1 with 250 μl/well of PBST for 3 times, and add samples to the 96-well plate according to Table 2:

TABLE 2

Preparation of solutions for biological determination experiment of E8

| Group | 2 μg/ ml CrylC toxin | E8 | Non-"β"-type Anti-Id ScFv | 2 × TY-AG liquid medium | CPBS |
|---|---|---|---|---|---|
| Experimental group 1 | 50 μl | 10 μl | | 40 μl | |
| Experimental group 2 | 50 μl | 30 μl | | 20 μl | |
| Experimental group 3 | 50 μl | 50 μl | | | |
| Positive control group | 50 μl | | | | 50 μl |
| Negative control group 1 | 50 μl | | 10 μl | 40 μl | |
| Negative control group 2 | 50 μl | | 30 μl | 20 μl | |
| Negative control group 3 | 50 μl | | 50 μl | | |

In Table 2, E8 is the supernate containing E8 primary culture obtained in Embodiment 2.

(c) Incubate the 96-well plate added with sample in step b at room temperature for 2 h, wash the plate with 250 μl/well of PBST for 3 times, add 100 μl/well of 10 μg/ml anti-Cry1C polyclonal antibody, then wash the plate with 250 μl/well of PBST for 3 times, add 100 μl/well of 1:5000 diluted HRP-goat anti-rabbit IgG and incubate it at room temperature for 1 h; wash the plate with 250 μl/well of PBST for 3 times, add 100 μl/well of substrate chromogenic solution, take reaction at room temperature for 10 to 20 min till blue appears and in the end add 50 μl/well of 2 mol/L H$_2$SO$_4$ to quickly terminate the reaction, and determine OD$_{450}$ by ELIASA.

Figure 2:
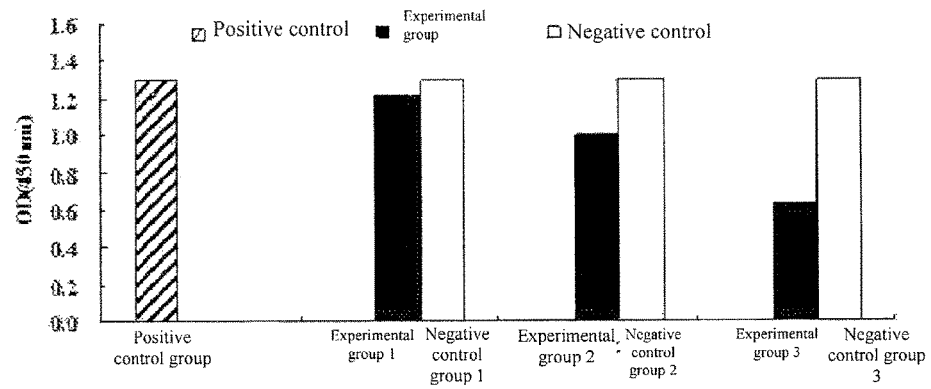
FIG. 2 is a schematic of E8 biological determination result.

The experimental result is shown in FIG. 2. Compared with positive control, anti-Cry1C toxin idiotype single-chain antibody E8 (experimental groups 1, 2 and 3) can inhibit the binding between Cry1C toxin and its receptor BBMV; non-"β"-type negative control does not have the phenomenon of inhibition, which further proves that E8 is "β" type.

Embodiment 4: Verify Insecticidal Activity of Anti-Cry1C Toxin Idiotype Single-Chain Antibody The experiment has experimental groups and control groups.

The experimental groups use the supernate (E8) containing E8 primary culture obtained in Embodiment 2.

The positive control groups adopt 0.2 g/L Cry1Ab toxin (CK+).

The negative control groups adopt non-"β" type Anti-Id ScFvs (CK−).

Experimental Procedure:

Take experimental groups, positive control groups and negative control groups each 10 ml, put them in sterilized culture dishes, add 6 paddy leaves and 6 cabbage leaves respectively, soak them for 30 min, take them out and dry them in the air; feed *Cnaphalocrocis medinalis* third instar larvae and *Plutella xylostella* third instar larvae with dried leaves.

Figure 3:
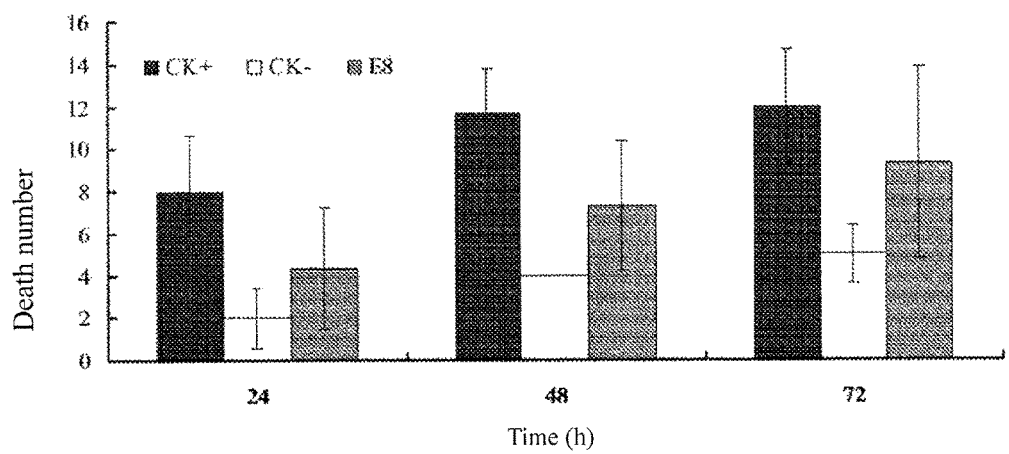
FIG. 3 is a schematic showing the death condition of *Cnaphalocrocis medinalis* third instar larvae after they were fed with paddy leaves soaked with E8, CK+ and CK− respectively.
Figure 4:
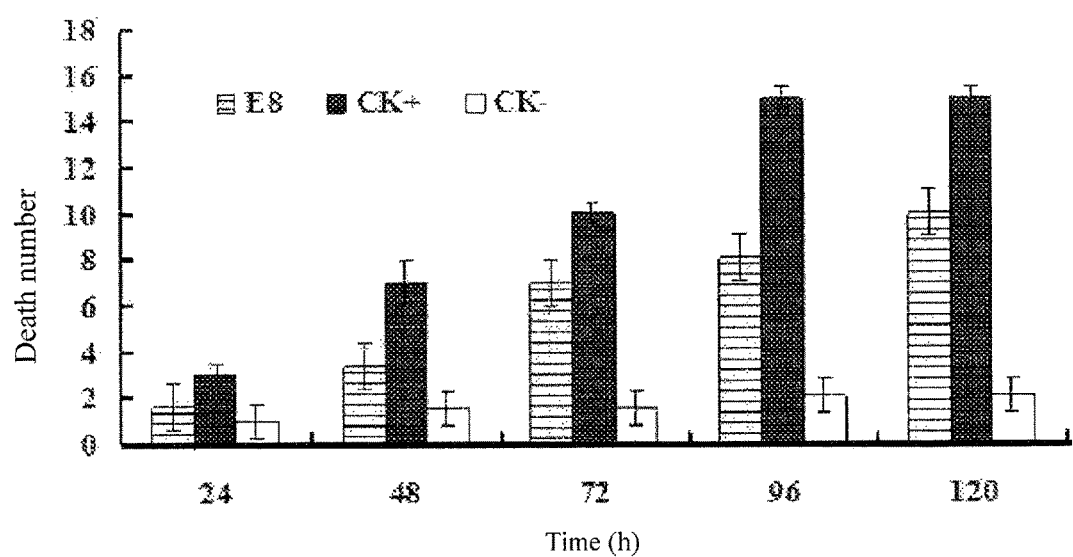
FIG. 4 is a schematic showing the death condition of *Plutella xylostella* third instar larvae after they were fed with cabbage leaves soaked with E8, CK+ and CK− respectively.

The experimental results are shown in FIG. 3 and FIG. 4. FIG. 3 shows the death condition of *Cnaphalocrocis medinalis* third instar larvae respectively fed with paddy leaves, which have been soaked with E8, Cry1Ab toxin (CK+) and non-"β"-type Anti-Id ScFvs (CK−). FIG. 4 shows the death condition of *Plutella xylostella* third instar larvae respectively fed with cabbage leaves, which have been soaked with E8, Cry1Ab toxin (CK+) and non-"β"-type Anti-Id ScFvs (CK−). It can be seen that E8 has a good insecticidal effect.

What is claimed is:

1. An insect-resistant gene, comprising the nucleotide sequence of SEQ ID NO: 1.

2. An anti-Cry1C toxin idiotype single-chain antibody encoded by the insect-resistant gene according to claim 1, wherein the antibody comprises the amino acid sequence of SEQ ID NO: 2.

3. A prokaryotic vector containing the insect-resistant gene according to claim 1.

4. An insecticide composition comprising the anti-Cry1C toxin idiotype single-chain antibody according to claim 2.

5. A method for controlling agriculture pests wherein said method comprises contacting the pests with a pesticidally effective amount of the anti-Cry1C toxin idiotype single-chain antibody according to claim 2.

* * * * *